United States Patent [19]

Martin et al.

[11] Patent Number: 4,560,701
[45] Date of Patent: * Dec. 24, 1985

[54] OXOTHIENOBENZOXEPINS, MEDICINAL USE, AND PROCESS FOR THE PREPARATION THEREOF

[75] Inventors: Lawrence L. Martin, Lebanon; Linda L. Setescak, Somerville, both of N.J.

[73] Assignee: Hoechst-Roussel Pharmaceuticals Inc., Somerville, N.J.

[*] Notice: The portion of the term of this patent subsequent to Jan. 29, 2002 has been disclaimed.

[21] Appl. No.: 503,456

[22] Filed: Jun. 13, 1983

Related U.S. Application Data

[63] Continuation-in-part of Ser. No. 285,897, Jul. 23, 1981, Pat. No. 4,496,580.

[51] Int. Cl.$^4$ .................. A61K 31/38; C07D 327/04; C07D 495/02; C07D 333/38
[52] U.S. Cl. ..................... 514/443; 514/448; 549/31; 549/50; 549/71; 549/44
[58] Field of Search .............. 549/31, 50, 71, 44; 424/275; 514/443, 448

[56] References Cited

U.S. PATENT DOCUMENTS 3,639,613  2/1972  Dunn et al. .............. 549/50
4,025,640  5/1977  McFadden et al. ......... 549/50
4,081,457  3/1978  McFadden et al. ......... 549/50
4,211,877  7/1980  Lee ..................... 549/50

FOREIGN PATENT DOCUMENTS 55-12477  9/1980  Japan .................... 549/50

OTHER PUBLICATIONS

Reichel et al., Z. Chem., III, 190 (1963).
Baird et al., J. Am. Chem. Soc., 84, 788 (1962).
Japanese Patent Abstract, 1, (No. 26, Sec. C), 1103 (1977).
Japanese Patent Abstract, 1, (No. 131, Sec. C), 2901 (1977).
Noller, Textbook of Organic Chemistry, W. B. Saunders Company, Philadelphia, 3rd. Ed., 1966, pp. 171 & 173.
Chem. Abs., 56, 456h (1962).
Yoshioka et al., J. Med. Chem., 21, 633 (1978).
Aultz et al., J. Med. Chem., 20, 1499 and 66 (1977).
Spinelli et al., J. Chem. Soc., 12, (Perkin 2) 1866 (1972).
Bourguignon et al., Compt. Rendu, 270 (5), 494 (1970).
Chem. Abs., 72, 90 162t (1970).

Primary Examiner—Henry R. Jiles
Assistant Examiner—Robert C. Whittenbaugh
Attorney, Agent, or Firm—Raymond R. Wittekind

[57] ABSTRACT

The invention relates to oxothienobenzoxepin compounds of the formula

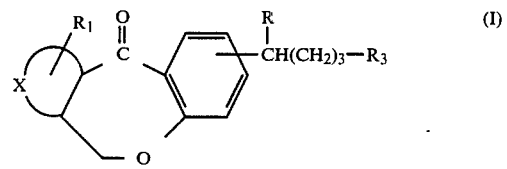

where
X together with the carbon atoms to which it is attached is a thiophene ring;
$R_1$ is hydrogen, a straight or branched chain alkyl group having 1 to 5 carbon atoms or a halogen atom;
$R_2$ is hydrogen or a straight chain alkyl group having 1 to 5 carbon atoms; and
$R_3$ is hydroxyl or

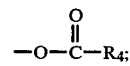

where $R_4$ is a straight chain or branched chain alkyl group having 1 to 10 carbon atoms, a phenyl group or a trifluoromethyl group. Methods for preparing the compounds and their use as antiinflammatory and analgesic agents are provided.

40 Claims, No Drawings

OXOTHIENOBENZOXEPINS, MEDICINAL USE, AND PROCESS FOR THE PREPARATION THEREOF

This application is a continuation-in-part of prior application Ser. No. 285,897, filed July 23, 1981 now U.S. Pat. No. 4,496,580.

This invention relates to oxothienobenzoxepin derivatives, mehods for their preparation and their use as antiinflammatory and analgesic agents.

A group of oxothienobenzoxepin compounds useful as antiinflammatory and analgesic agents is disclosed by Arthur R. McFadden et al in U.S. Pat. No. 4,025,640. The compounds are represented by the formula

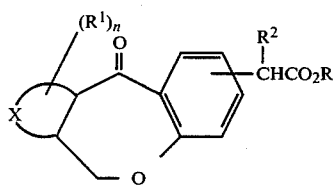

wherein X, together with the carbon atoms to which it is attached, is a 5 or 6-membered heteroaryl ring structure containing from 1 to 2 oxygen, nitrogen or sulfur atoms; R is hydrogen or straight or branched chain alkyl of from 1 to 5 carbon atoms; $R^1$ is hydrogen or lower alkyl of 1 to 4 carbon atoms, $R^2$ is hydrogen or methyl; and n is the integer 1, 2 or 3. When X together with the carbon atoms to which it is attached is a thiophene ring and when, R, $R^1$ and $R^2$ are each hydrogen, the resulting compounds are oxothienobenzoxepin acetic acids.

Another group of oxothienobenzoxepin compounds has now been discovered. These compounds are also useful as antiinflammatory and analgesic agents. In addition, these new compounds exhibit longer duration of action and lower ulcerogenicity then the oxothienobenzoxepin acetic acids and derivatives disclosed in U.S. Pat. No. 4,025,460.

More particularly, this invention provides compounds of the formula

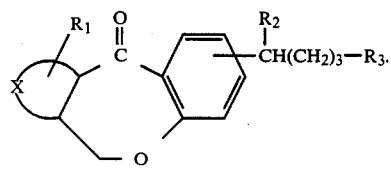

The substituent X together with the carbon atoms to which it is attached is a thiophene ring. The substituent $R_1$ is hydrogen, a straight or branched chain alkyl group having 1 to 5 carbon atoms or a halogen atom, preferably bromine; $R_2$ is hydrogen or a straight chain alkyl group having 1 to 5 carbon atoms; and $R_3$ is hydroxyl or

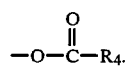

The substituent $R_4$ is a straight or branched chain alkyl group having 1 to 10 carbon atoms, a phenyl group or a trifluoromethyl group.

This invention also provides a method for preparing compounds of the following formula:

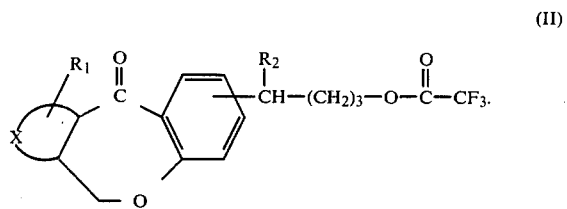

The substituent X together with the carbon atoms to which it is attached is a thiophene ring; $R_1$ is hydrogen, a straight or branched chain alkyl group having 1 to 5 carbon atoms or a halogen atom; and $R_2$ is hydrogen or a straight chain alkyl group having 1 to 5 carbon atoms. The method comprises reacting a compound of the formula

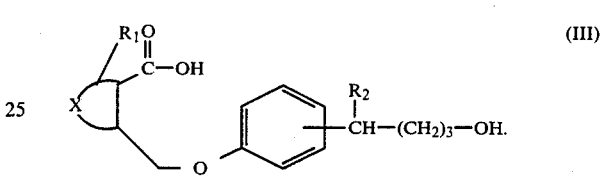

where $R_1$ and $R_2$ correspond to $R_1$ and $R_2$ in formula (II), with trifluoroacetic anhydride in solution at a temperature up to the reflux temperature of the reaction mixture.

In addition, this invention provides a method for preparing a compound of the formula

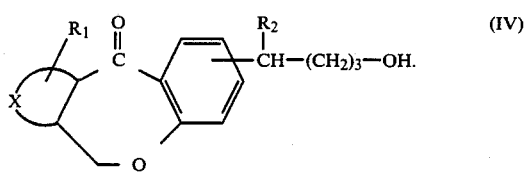

The method comprises hydrolyzing a compound of the formula

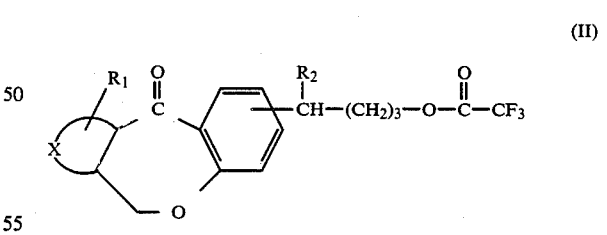

in acidic solution at a temperature up to the reflux temperature of the solvent employed in the solution. In formula (IV) and formula (II), X together with the carbon atoms to which it is attached is a thiophene ring; $R_1$ is hydrogen, a straight chain or branched chain alkyl group having 1 to 5 carbon atoms; and $R_2$ is hydrogen or a straight chain alkyl group having 1 to 5 carbon atoms.

Further, this invention provides a method of alleviating pain in a mammal by administering to a mammal a pain-alleviating effective amount of a compound of formula (I) above.

Still further, this invention provides a method of alleviating inflammation in a mammal by administering to a mammal an inflammation-alleviating effective amount of a compound of formula (I) above.

Finally, this invention provides a pharmaceutical composition comprising a compound of the invention and a pharmaceutically acceptable carrier therefor.

The compounds of this invention are represented generally by the foregoing formulae. Where the term alkyl is used in defining the substituents on these compounds, it is to be understood that the alkyl group is acyclic without unsaturation. Straight chain alkyl groups are preferred. It will also be understood that the group of compounds defined by formula (I) includes oxothieno[3,2-c]benzoxepins of the formula

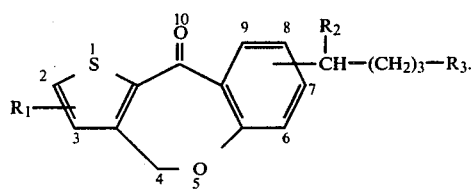
(IA)

where the

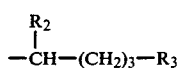

moiety is in the 7- or 8-position; oxothieno[3,4-c]benzoxepins of the formula

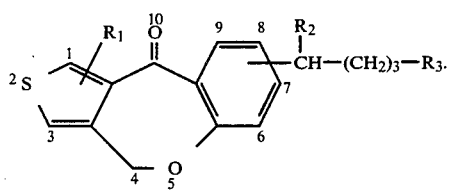
(IB)

where the

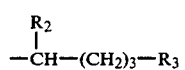

moiety is in the 7- or 8-position; and oxothieno[2,3-c]benzoxepins of the formula

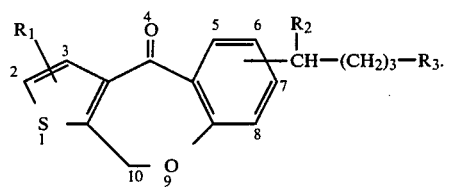
(IC)

where the

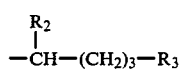

moiety is in the 6- or 7-position, and $R_1$, $R_2$ and $R_3$ correspond to the definition of $R_1$, $R_2$ and $R_3$, respectively, in formula (I). Among the preferred compounds of the invention are oxothienobenzoxepins in which $R_1$ is hydrogen and $R_2$ is hydrogen or a methyl group. When $R_4$ is an alkyl group, it is preferred that the alkyl group contain from 1 to 5 carbon atoms.

Another group of preferred compounds of this invention are compounds of formula (IA), where $R_1$ is hydrogen, a straight or branched chain alkyl group having 1 to 5 carbon atoms, $R_2$ is hydrogen or a straight chain alkyl group having 1 to 5 carbon atoms and $R_3$ is —OH or

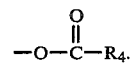

Particularly preferred are such compounds wherein $R_1$ and $R_2$ are each hydrogen.

The compounds of the present invention can be prepared in the following manner. The substituents $R_1$, $R_2$ and $R_3$ are as defined in connection with formula (I) unless otherwise indicated.

An alkyl thiophene ester of the formula

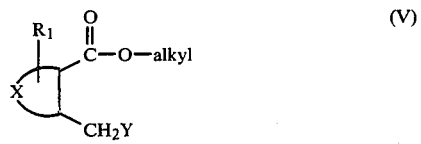
(V)

where X together with the carbon atoms to which it is attached is a thiophene ring, alkyl is a straight chain or branched alkyl group having 1 to 5 carbon atoms and Y is halogen, preferably bromine, is allowed to react with a m- or p-hydroxyphenyl alkanol of the formula

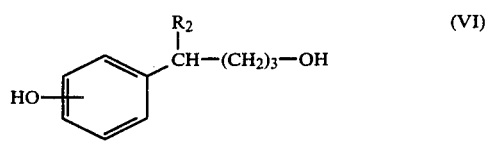
(VI)

to form an ester of the formula

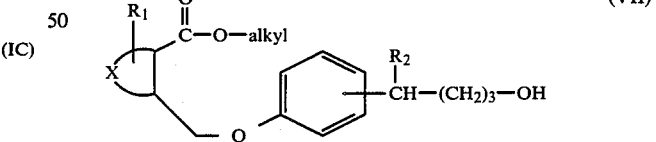
(VII)

For example, the oxothieno[3,2-c]benzoxepins of formula (IA) above can be prepared by reacting an alkyl thiophene ester of the formula

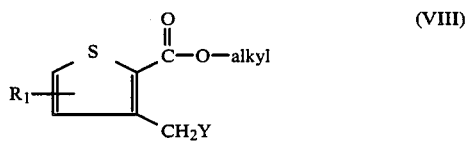
(VIII)

with a m- or p-hydroxyphenyl alkanol of the formula

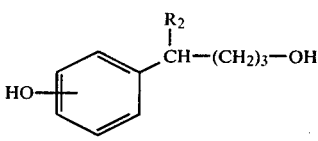

to form an ester of the formula

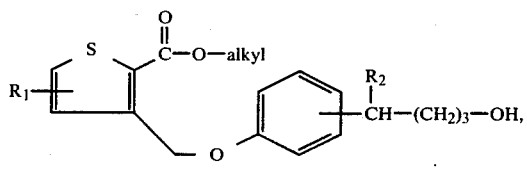

and the oxothieno[2,3-c]benzoxepins of formula (IC) above can be prepared by reacting an alkyl thiophene ester of the formula

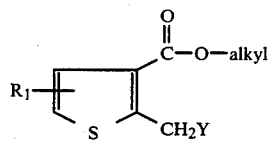

with a m- or p-hydroxyphenylalkanol of the formula (IX) to provide an ester of the formula

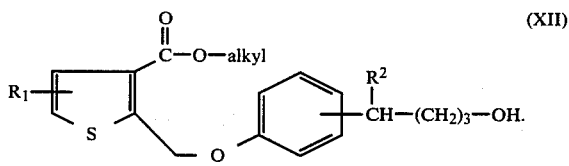

The reaction can be carried out in the presence of a solvent, such as acetone, butanone, ethanol or dimethylformamide. An acid scavenger, such as potassium carbonate or sodium ethoxide, is preferably employed. A reaction initiator, such as potassium or sodium iodide, is optional. The reaction is conveniently carried out at a temperature of about ambient temperature to the boiling point of the solvent for a few minutes to about 72 hours to provide a compound of formula (VII). The resulting compound can be separated from the reaction mixture and purified using well-known techniques.

The halogenated thiophene of formula (V) above can be prepared using conventional techniques. For example, a bromomethyl thiophene ester can be formed by esterifying a substituted or unsubstituted methyl thiophene carboxylic acid with an alkanol to provide the alkyl group in the compound of formula (V), and then brominating the resulting ester with N-bromosuccinimide. Substituted methyl thiophene carboxylic acids and methods for their preparation are known in the art. See, for example, U.S. Pat. No. 3,639,613, German Offenlegungsschrift No. 1,088,507 and D. Spinelli et al, *J. Chem. Soc.*, Perkin 2 1972 (12), 1866.

Another method that can be employed for selective bromination of the methyl group adjacent to the ester moiety in formula (V) involves a procedure analogous to a prior art method described generally in L. Reichel and W. Hempel, *Z, Chem.*, III, 190 (1963). This procedure employs a thienofuranone and phosphorus tribromide and bromine as reactants. The reaction involves simultaneous opening of the furanone ring and bromination of the methyl group on the resulting thiophene. Unsubstituted thienofuranones and their method of preparation are disclosed by J. Bourguignon et al, *C. R. Acad. Sci.* Paris, Ser. C 1970, 270 (5), 494-70. Alkyl substituted thienofuranones can be prepared by conventional techniques. For example, a 2-alkyl-substituted thiophene containing a reactive 4-bromine substituent can be reacted with n-butyllithium and formaldehyde to form a hydroxy-alkyl-substituted thiophene-lithio intermediate. Additional treatment with n-butyllithium and with dry ice followed by aqueous quenching affords a 5-alkyl-3-hydroxymethylthiophene-2-carboxylic acid, which can then be cyclized to form the alkyl-substituted thienofuranone.

The halogenated thiophene of formula (V) above can be prepared employing alternative conventional techniques. For example, lithiation of a 3-halothiophene with phenyllithium provides a 3-halo-2-lithiothiophene which can be carbonated by means of carbon dioxide to a 3-halothiophene-2-carboxylic acid, the carboxylic acid group of which can be reduced with diborane to a 3-halo-2-thiophenemethanol. Exchange of the halo group of a 3-halo-2-thiophenemethanol with an alkyllithium, such as n-butyllithium, gives a 3-lithio-2-thiophenemethanol which can be carbonated ($CO_2$) to a 2-hydroxymethyl-3-thiophenecarboxylic acid, the carboxylic acid group of which can be esterified with an alkanol in the presence of a mineral acid to an alkyl 2-hydroxymethyl-3-thiophenecarboxylate. Treatment of an alkyl 2-hydroxymethyl-3thiophenecarboxylate with a thionyl halide affords an alkyl 2-halomethylthiophenecarboxylate (V).

The m- or p-hydroxyphenyl alkanol can also be prepared using conventional techniques. For example, a m- or p-methoxyphenylbutyric acid can be reacted at reflux temperature with hydrogen bromide to form a m- or p-hydroxyphenylbutyric acid. This acid can then be reacted with borane in tetrahydrofuran to form m- or p-hydroxyphenylbutanol. This latter compound is reported in JACS, 84, 788 (1962).

Alternative conventional techniques can be employed to prepare the m- or p-hydroxyphenyl alkanols (IX). For example, a m- or p-nitrophenylbutyric acid can be esterified by means of an alkanol in the presence of a mineral acid to an alkyl m- or p-nitrophenylbutyrate which can be reduced with hydrogen in the presence of a metal catalyst, such a palladium-on-carbon to an alkyl m- or p-aminophenylbutyrate. Diazotization of an alkyl m- or p-aminophenylbutyrate followed by hydrolysis of the resulting diazonium salt affords an alkyl m- or p-hydroxyphenylbutyrate which can be reduced with borane methyl sulfide to a m- or p-hydroxyphenylalkanol (IX).

The ester of formula (VII) is saponified to form the corresponding carboxylic acid. The saponification reaction can be carried out according to conventional techniques. For example, the ester of formula (VII) can be reacted with a base, such as sodium or potassium hydroxide, in a solvent, such as aqueous ethanol or water. Typically, reaction can be carried out at a temperature of from about ambient temperature to the boiling point of the solvent for a period of about 15 minutes to about 24 hours.

The carboxylic acid formed by the saponification of the ester of formula (VII) is then cyclized by a method that will not interfere with the hydroxyl group on the side chain of the phenyl group or by a method in which the hydroxyl group is converted to another moiety that can be readily converted back to the hydroxyl group. One method involves acylating the carboxylic acid to convert the alcohol hydroxyl group to an ester, then cyclizing the acid, such as by treatment with a dehydrating agent, or by converting the carboxylic acid group of the acylated derivative to an acid chloride by reaction with thionyl chloride followed by cyclization using aluminum chloride. The acylation can be carried out using acyl halides or acid anhydrides under well-known reaction conditions to form esters.

A preferred method for preparing compounds in which $R_3$— is

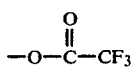

involves reacting a compound of formula (III) with trifluoroacetic anhydride. This reaction is conveniently carried out with about 2 to about 2.5 equivalents of the trifluoroacetic anhydride. Preferably, the trifluoroacetic anhydride is employed in about 15% stochiometric excess. The cyclization reaction can be carried out in a suitable solvent, such as dichloromethane or chloroform, at a temperature from about ambient temperature to the reflux temperature of the solvent. The reaction is conducted until substantially complete. This will take about 1 to about 8 hours, typically about 2 hours. The compound of formula (II) can be separated from the reaction mixture and purified according to conventional techniques.

This invention also includes compounds of the following formula

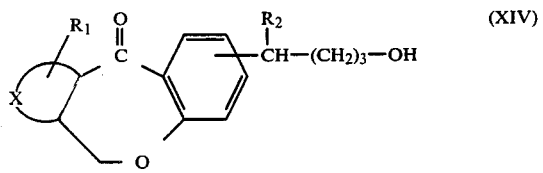

These compounds can be prepared by hydrolyzing compounds of formula (II) under acidic conditions. A strong mineral acid, such as sulphuric acid or hydrochloric acid, is suitable for this hydrolysis reaction. The acid of choice is hydrochloric acid. This reaction can be carried out by dissolving the reactants in a suitable solvent, such as acetone, methyl ethyl ketone or an aqueous alcohol, such as aqueous methanol, ethanol or propanol. The preferred solvent is acetone. The reaction is typically conducted at an elevated temperature, preferably the reflux temperature of the solvent. The reaction is carried out until substantial completion, which can be conveniently determined by chromatographic techniques. Typically, the reaction time will be about 4 to about 24 hours. The resulting oxothienobenzoxepin compounds can be separated from the reaction mixture and purified using well-known techniques. Compounds of the formula (XIV) can be readily converted to esters by acylation with acyl halides or acid anhydrides using standard reaction conditions.

Examples of some of the compounds of the invention are:
4-(4,10-dihydro-10-oxothieno[3,2-c][1]benzoxepin-8-yl)butyl butyrate;
4-(4,10-dihydro-10-oxothieno[3,2-c][1]benzoxepin-8-yl)butyl hexanoate;
4-(4,10-dihydro-10-oxothieno[3,2-c][1]benzoxepin-8-yl)butyl 2,2-dimethylpropionate;
4-(4,10-dihydro-10-oxothieno[3,2-c][1]benzoxepin-8-yl)butyl benzoate;
4-(4,10-dihydro-10-oxotheno[3,2-c][1]benzoxepin-8-yl)pentanol;
4-(4,10-dihydro-10-oxothieno[3,2-c][1]benzoxepin-8-yl)pentyl butyrate;
4-(4,10-dihydro-10-oxothieno[3,2-c][1]benzoxepin-7-yl)butanol;
4-(4,10-dihydro-10-oxothieno[3,2-c][1]benzoxepin-7-yl)butyl acetate;
4-(4,10-dihydro-10-oxothieno[3,2-c][1]benzoxepin-7-yl)pentanol;
4-(4,10-dihydro-10-oxothieno[3,4-c][1]benzoxepin-8-yl)butanol;
4-(4,10-dihydro-10-oxothieno[3,4-c][1]benzoxepin-8-yl)butyl acetate;
4-(4,10-dihydro-10-oxothieno[3,4-c][1]benzoxepin-8-yl)pentanol;
4-(4,10-dihydro-10-oxothieno[3,4-c][1]benzoxepin-7-yl)butanol;
4-(4,10-dihydro-10-oxothieno[2,3-c][1]benzoxepin-6-yl)butanol;
4-(4,10-dihydro-10-oxothieno[2,3-c][1]benzoxepin-6-yl)butyl acetate;
4-(4,10-dihydro-10-oxothieno[2,3-c][1]benzoxepin-6-yl)pentanol;
4-(4,10-dihydro-10-oxothieno[2,3-c][1]benzoxepin-7-yl)butanol;
4-(4,10-dihydro-2-methyl-10-oxothieno[3,2-c][1]benzoxepin-8-yl)butanol; and
4-(2-bromo-4,10-dihydro-10-oxothieno[3,2-c][1]benzoxepin-8-yl)butanol.

The compounds of the present invention are useful as systemic antiinflammatory agents due to their ability to suppress inflammation in mammals. The activity of the compounds is demonstrated in the carrageenan-induced rat paw edema antiinflammatory assay. (The carrageenan-induced rat paw edema test is hereinafter referred to as CPE).

The compounds of the present invention are also useful as analgesic agents due to their ability to alleviate pain in mammals. This activity of the compounds is demonstrated in the 2-phenyl-1,4-benzoquinone-induced writhing test in mice. (The phenylquinone-induced writhing test is hereinafter referred to as PQW).

The compounds of the present invention also exhibit surprisingly low ulcerogenic activity. (The ulcerogenic activity test is hereafter referred to as GI). The CPE, PQW and GI test methods are reported at *J. Med, Chem.*, 20, 66, 69 (1977). These tests have been used to compare the compounds of the present invention with related compounds disclosed in U.S. Pat. No. 4,025,640. The results are reported in the following Table. Compounds 1 and 2 in the following Table are compounds of the patent. Compounds 3 and 4 are compounds of the present invention.

TABLE

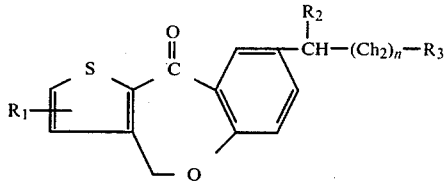

| Compound | $R_1$ | $R_2$ | $R_3$ | n | $ED_{50}$ mg/kg of body weight PQW | $ED_{50}$ mg/kg of body weight CPE | $ID_{50}$ mg/kg of body weight GI |
|---|---|---|---|---|---|---|---|
| 1 | H | H | —COOH | 0 | 4.5 | 3.4 | 33.7 |
| 2 | H | H | —C(=O)—O(CH)(CH$_3$)CH$_3$ | 0 | 13.7 | 1.6 | 21.6 |
| 3 | H | H | —OH | 3 | 7.4 | 8.6 | >400 |
| 4 | H | H | —O—C(=O)—CF$_3$ | 3 | 9.1 | 6.5 | 300 |

The data in the Table confirm that compounds 3 and 4 of the invention exhibit activity in the CPE and PQW tests; that is, they are useful as antiinflammatory and analgesic agents. Surprisingly, compounds 3 and 4 exhibit a very low incidence of ulcers in test animals at very high dosage levels.

Effective amounts of the compounds of the present invention may be administered to a subject by one of various methods, for example, as solutions or suspensions, and in some cases intravenously in the form of sterile solutions.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troaches, capsules, elixirs, suspensions, syrups, wafers, chewing gums and the like. These preparations should contain as the active ingredient, at least about 0.5% by weight of the compounds of the invention. The amount of active ingredient may be varied depending upon the particular form and may conveniently be between about 4 and about 70% by weight of a dosage unit. The amount of the compound present in such compositions is such that a suitable dosage will be obtained. Preferred compositions and preparations according to the present inventions are prepared so that an oral dosage unit form contains between about 10 and about 500 milligrams of the compounds of the invention.

The tablets, pills, capsules, troaches and the like may also contain the following adjuvants: a binder, such as microcrystalline cellulose, gum tragacanth or gelatin; and excipient, such as starch or lactose; a disintegrating agent, such as alginic acid, Primogel, corn starch and the like; a lubricant, such as magnesium stearate or Sterotex; a glidant, such as colloidal silicon dioxide; a sweetening agent, such as sucrose or saccharine; or a flavoring agent, such as peppermint, methyl salicylate or orange flavoring. When the dosage unit form is a capsule, it may contain, in addition to materials of the above type, a liquid carrier, such as a fatty oil. Other dosage unit forms may contain other various materials that modify the physical form of the dosage unit, for example, as coatings. Thus, tablets or pills may be coated with sugar, shellac or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain as active ingredient, at least about 0.1% by weight of the compounds of the invention. Typically, the amount of active ingredient will be between about 0.5 and about 30% by weight of a dosage unit. The amount of the inventive compound present in such compositions is such that a suitable dosage will be obtained. Preferred compositions and preparations according to the present invention are prepared so that a parenteral dosage unit contains between about 0.5 and about 100 milligrams of the compounds of the invention.

The solutions or suspensions may also include the following adjuvants: a sterile diluent, such as water for injection, saline solution, fixed oils, polyethylene glycols, glycerine, propylene glycol or other synthetic solvents; antibacterial agents, such as benzyl alcohol or methyl paraben; antioxidants, such as ascorbic acid or sodium bisulfite; chelating agents, such as ethylene diaminetetraacetic acid; buffers, such as acetates, citrates or phosphates; and agents for the adjustment of tonicity, such as sodium chloride or dextrose. The parenteral preparation can be enclosed in ampules, disposable syringes or multiple dose vials made of glass or plastic.

This invention will now be described in greater detail in the following Examples, in which all parts, proportions, percentages and ratios are by weight unless otherwise indicated.

EXAMPLE 1

3-[4-(1Hydroxylbutyl)phenoxy-methyl]-2-thiophenecarboxylic acid ethyl ester

A stirred mixture of 3.32 g (0.02 mol) of 4-(4-hydroxyphenyl)-1-butanol, 11.06 g (0.08 mol) of anhydrous K$_2$CO$_3$, 0.2 g of KI, 4.70 g (0.02 mol) of 3-bromomethyl-2-thiophenecarboxylic acid methyl ester and 100 ml of 2-butanone was heated 24 hours under reflux. The mixture was vacuum filtered and the filtrate was concentrated to an oil which crystallized. A solution of the material and 70 ml of CH$_2$Cl$_2$ was washed with 10% NaOH, dried (Na$_2$SO$_4$) and concentrated to an oil which crystallized on trituration with hexane. The crude material (6.0 g) was extracted with hot (55° C.) cyclohexane (400 ml) to afford 2.15 g (33.6%) of colorless crystals, m.p. 67°–68.5° C. The material appeared pure by TLC (silica gel, ethylacetate, R$_f$=0.58; 20% methanol/toluene, R$_f$=0.41) and the IR (CHCl$_3$), $^1$H-NMR (CDCl$_3$) and MS (M+, 320) were consistent with structure.

Analysis: Calculated for C$_{17}$H$_{20}$O$_4$S: 63.73%C; 6.29%H; Found: 63.45%C; 6.30%H.

EXAMPLE 2

3-[4-(1-Hydroxybutyl)phenoxy-methyl]-2-thiophenecarboxylic acid

A stirred solution of 30.3 g (0.54 mol) of KOH, 30 ml of water, 17.26 g (0.054 mol) of crude 3-[4-(1-hydroxybutyl)phenoxy]methyl-2-thiophenecarboxylic acid methyl ester and 200 ml of 95% ethanol was heated under reflux. Thin layer analysis (silica gel, ethyl acetate) indicated the hydrolysis was complete after three hours. The ethanol was removed on a rotary evaporator and the residual syrup was diluted with 200 ml of water and extracted with 100 ml of ether. The aqueous phase was acidified with 50 ml of concentrated hydrochloric acid and with ice water cooling. A yellow solid separated and was collected by vacuum filtration. Thorough washing with water and drying in vacuo at 40° C. over NaOH pellets afforded 9.33 g of yellow solid. Recrystallization from 20 ml of 95% ethanol afforded 5.52 g (31.9%) of cream colored material, m.p. 144.5°–146° C. The material appeared pure by TLC (silica gel, acetic acid, $R_f=0.76$; alumina, dimethylformamide, $R_f=0.17$) and the IR (KBr), $^1$H-NMR (DMSO-d$_6$) and MS (M+,306) were consistent with structure.

Analysis: Calculated for $C_{16}H_{18}O_4S$: 62.73%C; 5.92%H. Found: 62.83%C; 5.91%H.

EXAMPLE 3

4-(4,10-Dihydro-10-oxothieno[3,2-c][1]benzoxepin-8-yl)-butyl trifluoroacetate A stirred suspension of 14.33 g (0.468 mol) of 3-[4-(1-hydroxybutyl)phenoxy]methyl-2-thiophenecarboxylic acid and 150 ml of anhydrous $CH_2Cl_2$ was treated with one portion of trifluoroacetic anhydride (22.60 g, 0.107 mol). The suspended material rapidly dissolved and the stirred solution was heated under reflux for four hours. After standing two days at ambient temperature, the reaction was quenched with water (70 ml) and washed with 50 ml of 5% NaHCO$_3$ solution. The dried (Na$_2$SO$_4$) organic phase was concentrated to an oil, which was further dried by azeotropic distillation of toluene. The oil was dissolved in approximately 15 ml of isopropanol, seeded with product previously prepared on a smaller scale, and stirred until a thick crystalline mass formed. The mass was triturated with isopropanol, followed by vacuum filtration. The filter cake was dried in vacuo at 40° C. to afford 15.08 g (83.8%) of almost colorless crystals, m.p. 65.5°–67° C. The material appeared pure by TLC (siica gel, ethyl acetate, $R_f=0.70$; dichloromethane, $R_f=0.51$) and the IR (KBr), $^1$H-NMR (CDCl$_3$) and MS (M+, 384) were consistent with structure.

Analysis: Calculated for $C_{18}H_{15}F_3O_4S$: 56.25%C; 3.93%H. Found: 56.36%C; 3.94%H.

EXAMPLE 4

4-(4,10-Dihydro-10-oxothieno[3,2-c][1]benzoxepin-8-yl)butanol

A stirred solution of 11.42 g (0.0297 mol) of 4-(4,10-dihydro-10-oxothieno[3,2-c][1]benzoxepin-8-yl)butyl trifluoroacetate, 480 ml of acetone and 250 ml of 5% hydrochloric acid was heated 20.5 hours under reflux. The cooled solution was concentrated to remove the acetone and the residual biphasic mixture was extracted with ether. The organic phase was washed with 5% NaHCO$_3$, dried (Na$_2$SO$_4$), filtered and concentrated to turbid oil. The oil was subjected to azeotropic distillation with toluene to afford a clear amber oil (9.82 g). A solution of the oil and 20 ml of warm toluene was diluted to the cloud point with cyclohexane, seeded with crystals obtained from a small scale trial recrystallization and stirred. More cyclohexane was added and the resulting mixture was stirred several minutes until solidification was complete. The mixture was allowed to stand overnight at ambient temperature. The material was isolated by vacuum filtration, washed with cyclohexane and dried in vacuo (pump) at ambient temperature to afford 7.73 g (90.2%) of a colorless waxy solid, m.p. 52°–54° C. The material appeared pure by TLC (silica gel, ethyl acetate, $R_f=0.49$; acetonitrile, $R_f=0.71$) and the IR (KBr), $^1$H-NMR (CDCl$_3$) and MS (MH+,289) were consistent with structure.

Elemental analysis: Calculated for $C_{16}H_{16}O_3S$: 66.64%C; 5.59%H. Found: 66.49%C; 5.51%H.

EXAMPLE 5

4-(4,10-Dihydro-10-osothieno[3,2-c][1]benzoxepin-8-yl)butyl acetate

A stirred solution of 4-(4,10-dihydro-10-oxothieno[3,2-c][1]benzoxepin-8-yl)butanol (8.07 g, 0.028 mol) and sieve-dried pyridine (25 ml) was treated over 0.5 min. with acetic anhydride (8.58 g, 0.084 mol). The solution was stirred for 165 min. at ambient temperature and was then heated on a steam bath for 15 minutes. The hot solution was decanted into water (150 ml) (lower phase yellow oil separated), and the mixture was extracted with dichloromethane (70 ml). The organic phase was washed with 5% hydrochloric acid, water and 5% sodium bicarbonate. The dried (Na$_2$SO$_4$) organic phase was concentrated to an oil, which was further dried by azeotropic distillation of toluene. A small portion of the oil was titurated on a watch glass to afford seed crystals. The main portion of the oil was triturated with hexane and seeded to afford a crystalline solid (8.08 g, 87.3%), m.p. 53.5°–55° C. The material appeared pure by TLC (silica gel, CH$_2$Cl$_2$, $R_f=0.18$; ethyl acetate, $R_f=0.63$) and the IR (CHCl$_3$), $^1$H-NMR (CDCl$_3$) and MS (M+,330) were consistent with structure.

Elemental analysis: Calculated for $C_{18}H_{18}O_4S$: 65.44%C; 5.49%H. Found: 65.45%C; 5.49%H.

EXAMPLE 6

Ethyl 4-(4-nitrophenyl)pentanoate

A mixture of 110 g of 4-(4-nitrophenyl)valeric acid, 660 ml of absolute ethanol and 10 ml of concentrated sulfuric was heated under reflux overnight. The ethanol was evaporated in vacuo and the residue was partitioned between ether and water. The ether extract was washed with 5% sodium bicarbonate, with water, dried over anhydrous sodium sulfate, filtered and evaporated to give 119 g (97%) of product. The product has bp 127°–128° C. (1.5 mm).

Analysis: Calculated for $C_{13}H_{17}NO_4$: 62.14%C; 6.82%H; 5.58%N. Found: 62.28%C; 6.92%H; 5.45%N.

EXAMPLE 7

Ethyl 4-(4-aminophenyl)pentanoate

A mixture of 114 g of ethyl 4-(4-nitrophenyl)pentanoate, 170 ml of absolute ethanol and 2 g of 10% palladium-on-charcoal, was hydrogenated (Paar shaker) until consumption of hydrogen ceased. The catalyst was filtered and the ethanol evaporated. The residue was partitioned between water and ether. The ether extract was washed with 5% sodium bicarbonate and water. The ether extract was dried over anhydrous sodium sulfate, filtered and evaporated to give an oil. The oil was distilled 0.55-0.60 mm to give 85 g (86%) of product, b.p. 118°-122° C.

Analysis: Calculated for $C_{13}H_{19}NO_2$: 70.56%C; 8.65%H; 6.33%N. Found: 70.69%C; 8.64%H; 6.18%N.

EXAMPLE 8

Ethyl 4-(4-hydroxyphenyl)pentanoate

To a solution of 350 g of concentrated sulfuric acid and 350 ml of water cooled to 0° C., 40 g of ethyl 4-(4-aminophenyl)pentanoate was added dropwise, maintaining the temperature at 0°-2° C. The mixture was then treated dropwise with 13.66 g of sodium nitrite in 25 ml of water at such a rate that the temperature did not exceed 2° C. The resultant solution was added dropwise to a refluxing solution of 387 g of copper sulfate in 600 ml of water over a period of approximately 30 minutes. The mixture was refluxed an additional 10 minutes, cooled to room temperature, and 800 ml of water was added. The mixture was extracted thrice with dichloromethane (additional water was needed to dissolve the salts). The organic phase was washed with water, dried over anhydrous sodium sulfate, filtered and evaporated to give an oil. The oil was distilled at 0.6 mm to give 21.05 g (53%) of product, b.p. 129° C., which crystallized on cooling, m.p. 32°-34° C.

Analysis: Calculated for $C_{13}H_{18}O_3$: 70.25%C; 8.16%H. Found: 69.98%C; 8.19%H.

EXAMPLE 9

4-(4-Hydroxyphenyl)pentanol

A three-necked flask containing 30 g of ethyl 4-(4-hydroxy)pentanoate in 150 ml of toluene (sieve dried) under an atmosphere of nitrogen was placed in a water bath. The temperature was maintained between 20°-25° C. while 270 ml of 1M borane-methyl sulfide/dichloromethane solution was added dropwise over a 15 minute period. The water bath was removed and the mixture was heated under reflux overnight. The mixture was cooled and 200 ml of cold methanol was added cautiously. Nitrogen was bubbled through the mixture for one hour. The solvents were evaporated and the residue was partitioned between ether and water. The ether extract was dried over anhydrous sodium sulfate, filtered and evaporated to give an oil which was chromatographed on a Waters Associates Prep LC—System 500 (two silica gel columns, 60% hexane:40% ethyl acetate) to give 13.7 g (57%) of product.

Analysis: Calculated for $C_{11}H_{16}O_2$: 73.30%C; 8.95%H. Found: 72.96%C; 8.80%H.

EXAMPLE 10

4-[4-(2-Carbomethoxy-3-thienylmethoxy)phenyl]pentanol

A stirred suspension of 8.0 g of 4-(4-hydroxyphenyl)pentanol, 18.41 g of anhydrous potassium carbonate, 0.4 g of potassium iodide, 10.44 g of methyl 3-bromomethyl-2-thiophenecarboxylate, and 225 ml of 2-butanone was heated under reflux overnight, with exclusion of moisture. The mixture was filtered while hot and the filter cake was washed with 2-butanone. The combined filtrate was concentrated, and a solution of the residue and dichloromethane was washed with 10% sodium hydroxide solution, water and saturated brine. The dried (over anhydrous sodium sulfate) organic phase was filtered and the filtrate was concentrated to an oil. Purification by high-pressure liquid chromatography (Waters Associates Prep LC/System 500A; two silica gel columns; 0.2 l/min flow rate; Gow Mac model 80-800 UV detector; 30% V/V ethyl acetate in hexane) gave 11.23 g (75.6%) of product as an oil, dried at 60° C. for 2 hours.

Analysis: Calculated for $C_{18}H_{22}O_4S$: 64.65%C; 6.63%H. Found: 64.79%C; 6.70%H.

EXAMPLE 11

4-[4-(2-Carboxy-3-thienylmethoxy)phenyl]pentanol

To a stirred solution of 14.59 g of potassium hydroxide, 15 ml of water, and 60 ml of 95% ethanol was added a solution of 8.68 g of 4-[4-(2-carbomethoxy-3-thienylmethoxy)phenyl]pentanol and 30 ml of 95% ethanol. The stirred solution was heated under reflux for five hours, allowed to stand overnight at ambient temperature, and concentrated. The residue was diluted with 500 ml of water, and the solution was acidified with concentrated hydrochloric acid. An oil separated. The mixture was extracted with ether (2×250 ml) and the combined organic phase was dried over anhydrous sodium sulfate, filtered and concentrated. A solution of the residue and toluene was filtered through anhydrous sodium sulfate and the filtrate was concentrated to afford 6.89 g (82.7%) of product as an oil, dried at 60° C. in vacuo.

Analysis: Calculated for $C_{17}H_{20}O_4S$: 63.73%C; 6.29%H. Found: 64.05%C; 6.33%H.

EXAMPLE 12

4-(4,10-Dihydro-10-oxothieno[3,2-c][1]benzoxepin-8-yl)pentyl trifluoroacetate

A stirred suspension of 4.18 g of 4-[4-(2-carboxy-3-thienylmethoxy)penyl]pentanol and 40 ml of sieve dried dichloromethane was treated in one portion with 6.30 g of trifluoroacetic anhydride. The resultant solution was heated for four hours under reflux with exclusion of moisture. The cooled solution was treated with 10 ml of water and stirred for ten minutes at ambient temperature. The phases were separated and the organic phase was washed with 5% sodium bicarbonate solution and saturated brine, dried over anhydrous sodium sulfate, filtered and concentrated. The residue was heated at 40° C. under high vacuum to afford 4.80 g (92.7%) of product as an oil.

Analysis: Calculated for $C_{19}H_{17}F_3O_4S$: 57.28%C; 4.30%H. Found: 57.42%C; 4.35%H.

EXAMPLE 13

4-(4,10-Dihydro-10-oxothieno[3,2-c][1][benzoxepin-8-yl)pentanol

A stirred solution of 16.0 g of 4-(4,10-dihydro-10-oxothieno[3,2-c][1]benzoxepin-3-yl)pentyl trifluoroacetate, 400 ml of acetone and 200 ml of 5% hydrochloric acid was refluxed for 4 hours and then allowed to stand overnight at ambient temperature. The solution was concentrated and the residual aqueous phase was extracted with ether (2×200 ml). The organic phase was washed with 100 ml of 5% sodium bicarbonate solution and 100 ml of saturated sodium chloride solution. The dried (over anhydrous sodium sulfate) organic phase was concentrated. The oily residue was dissolved in toluene and the solution was filtered through anhydrous sodium sulfate. The filtrate was concentrated to an oil. The oil was subjected to high-pressure liquid chromatography purification (Waters Associates Prep LC/System 500, two silica gel columns, 0.2 l/min flow rate, samples applied as a solution in 50% (vol/vol) ethyl acetate in hexane, eluted with 40% (vol/vol) ethyl acetate in hexane, Gow Mac UV detector). The appropriate fractions were combined and concentrated to an oil, which was dried in vacuo at 75° C. to afford 8.78 g (72.6%) of product, as an oil.

Analysis: Calculated for $C_{17}H_{18}O_3S$: 67.53%C; 6.00%H. Found: 67.75%C; 6.04%H.

EXAMPLE 14

3-Bromo-2-thiophenemethanol a. 3-Bromo-2-thiophenecarboxylic acid

A stirred, ice-water chilled solution of 16.3 g of 3-bromothiophene and 100 ml of anhydrous ether was treated dropwise, under nitrogen, over 70 minutes with of 50 ml of phenyllithium in ether (2.0M solution), with exclusion of moisture. After stirring at ambient temperature for 1.5 hours, the solution was decanted into dry ice and 200 ml of anhydrous ether. The mixture was stirred and a small amount of dry ice was added. The suspension was treated with water and 10% sodium hydroxide solution to pH=10. The phases were separated and the aqueous phase was extracted once with ether, and acidified with concentrated hydrochloric acid. The mixture was extracted with ether and the dried (over anhydrous sodium sulfate) organic phase was filtered and concentrated. Recrystallization of the residue from acetonitrile gave 10.38% g (50%) of product, m.p. 193°–196° C.

b. 3-Bromo-2-thiophenemethanol

A stirred, ice-water chilled solution of 90.0 g of 3-bromo-2-thiophenecarboxylic acid and 600 ml of sieve dried tetrahydrofuran was treated at 5° C. with 962 ml of borane in tetrahydrofuran (1.04M solution) over 2 hours (nitrogen atmosphere), with exclusion of moisture. The stirred solution and cooling bath were allowed to equilibrate to ambient temperature overnight. The stirred, chilled (10° C.) solution was treated dropwise with 150 ml methanol over 2 hours and then with 100 ml of 10% sodium hydroxide. After concentration, the residue was diluted with water, adjusted to pH=8 with 10% sodium hydroxide solution and extracted with ether (2×300 ml). The combined dried (over anhydrous sodium sulfate) ethereal phase was concentrated. Distillation gave 61 g (73%) of product, b.p. 79°–82° C. (0.38 mm).

Analysis: Calculated for $C_5H_5BrOS$: 31.11%C; 2.61%H. Found: 31.30L %C; 2.70%H.

EXAMPLE 15

2-[4-(4-Hydroxybutyl)phenoxymethyl]-3-thiophenecarboxylic acid methyl ester

To a stirred mixture of 8.31 g of 4-(4-hydroxyphenyl)-butanol, 20.73 g of milled anhydrous potassium carbonate, 0.5 g of powdered potassium iodide and 200 ml of 2-butanone was added, over a few minutes, a solution of 9.45 g 2-chloromethyl-3-thiophenecarboxylic acid methyl ester and 20 ml of 2-butanone. The suspension was heated under reflux overnight, with stirring. The reaction mixture was filtered while hot, and the filter cake was washed with 2-butanone. The combined filtrate was concentrated. The residue was dissolved in 200 ml of dichloromethane, and the solution was washed with 200 ml of 5% sodium hydroxide solution, 200 ml of water and then saturated brine solution. The dried (over anhydrous sodium sulfate) organic phase was filtered and concentrated. The residue was purified by high-pressure liquid chromatography (Water Associates Prep LC/System 500; two silica gel columns; sample applied as a filtered solution in 200 ml of dichloromethane using a little pure dichloromethane to flush the material onto the column before elution; eluted with 10% (V/V) ethylacetate in dichloromethane; 150 ml/min. flow rate maintained until major component began to elute, then increased flow rate to 250 ml/min; U.V. and refractive index detectors used) to afford 10.38 g (65.3%) of product, m.p. 58°–60° C., after concentration and trituration of the eluents with hexane.

Analysis: Calculated for $C_{17}H_{20}O_4S$: 63.73%C; 6.29%H. Found: 63.97%C; 6.48%H.

EXAMPLE 16

2-[4-(4-Hydroxybutyl)phenoxymethyl]-3-thiophenecarboxylic acid

A stirred solution of 7.96 g of 2-[4-(4-hydroxybutyl)-phenoxymethyl]-3-thiophenecarboxylic acid methyl ester, 14.41 g of potassium hydroxide, 15 ml of water and 100 ml of 95% ethanol was refluxed for one hour. The solution was concentrated. The residue was diluted with 200 ml of water and the solution was extracted once with ether. The aqueous phase was acidified with concentrated hydrochloric acid, with cooling, and the precipitate was collected, washed with water and dried in vacuo at 40° C. overnight over sodium hydroxide pellets. Recrystallization from 20 ml of 95% ethanol gave 6.62 g (88%) of product, m.p. 139.5°–141° C.

Analysis: Calculated for $C_{16}H_{18}O_4S$: 62.73%C; 5.92%H. Found: 62.52%C; 5.96%H.

EXAMPLE 17

4-(4,10-Dihydro-4-oxothieno[2,3-c][1]benzoxepin-6-yl)butyl trifluoroacetate

To a suspension of 4.40 g of 2-[4-(4-hydroxybutyl)-phenoxymethyl]-3-thiophenecarboxylic acid and 80 ml of sieve dried dichloromethane, was added, over a few seconds, 6.66 g of trifluoroacetate anhydride with stirring. The solution was refluxed for 1.5 hours, additional trifluoroacetic anhydride (2.2 g) was added, and the solution refluxed overnight, with the exclusion of moisture. To the cooled solution, was added 15 ml of water, and the mixture was stirred at ambient temperature for 15 minutes. The mixture was diluted with dichloromethane and washed with water and 5% sodium bicarbonate solution. The dried (over anhydrous sodium sulfate) organic phase was filtered and concentrated. The residue was dissolved in isopropanol (15 ml) with warming. After standing for 3 hours the precipitate was collected, washed with isopropanol and dried in vacuo at ambient temperature to give 4.08 g (73.7%) of product, m.p. 65.5°–67.5° C.

Analysis: Calculated for $C_{18}H_{15}F_3O_4S$: 56.25%C; 3.93%H. Found: 56.34%C; 3.89%H.

EXAMPLE 18

4-(4,10-Dihydro-4-oxothieno[2,3-c][1]benzoxepin-6-yl)butanol

A stirred solution of 7.74 g of 4-(4,10-dihydro-4-oxothieno[2,3-c][1]benzoxepin-6-yl)butyl trifluoroacetate, 385 ml of acetone and 200 ml of 5% hydrochloric acid was heated under reflux for 1.25 hours. The solution was concentrated and the residue was extracted with ether (2×150 ml). The combined organic phase was washed with 5% sodium bicarbonate solution, dried over anhydrous sodium sulfate, filtered and concentrated. The residue was dissolved in 70 ml of toluene and the mixture was filtered through anhydrous sodium sulfate. The filter cake was washed with 50 ml of toluene and the combined filtrate was concentrated. The residue was purified by high-pressure liquid chromatography (Waters Associates Prep LC/System 500A, one silica gel column, eluted with ether, 100 ml/min flow rate, Gow Mac UV detector). The desired fractions were combined and concentrated to give an oil. The oily residue was triturated with hexane, seeded with authentic crystalline product obtained by triturating a sample of the oil on a watch glass. The oil was triturated with fresh hexane, and chilled in an ice-water bath. The hexane was decanted and the residue was triturated to give 4.39 g (75.7%) of product, dried in vacuo with exclusion of light for 48 hours at ambient temperature.

Analysis: Calculated for $C_{16}H_{16}O_3S$: 66.64%C; 5.59%H. Found: 66.35%C; 5.64%H.

What is claimed is:

1. A compound of the formula

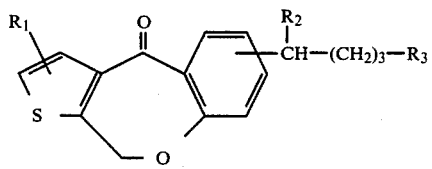

where $R_1$ is hydrogen or a straight or branched chain alkyl group having 1 to 5 carbon atoms, $R_2$ is hydrogen or a straight chain alkyl group having 1 to 5 carbon atoms, $R_3$ is OH or

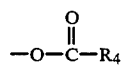

where $R_4$ is a straight or branched chain alkyl group having 1 to 10 carbon atoms, phenyl or trifluoromethyl.

2. A compound according to claim 1 which comprises

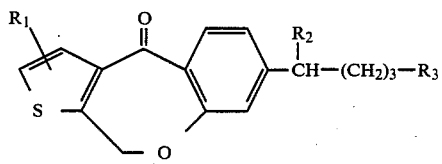

where $R_1$, $R_2$, $R_3$ and $R_4$ are as defined.

3. A compound according to claim 1 which comprises

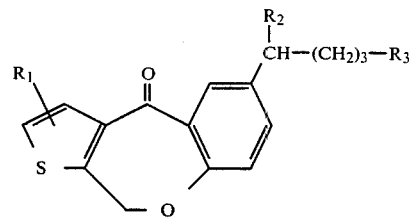

where $R_1$, $R_2$, $R_3$ and $R_4$ are as defined.

4. A compound according to claims 1, 2, or 3 wherein $R_3$ is

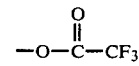

or OH.

5. A compound according to claims 1, 2 or 3 wherein $R_1$ and $R_2$ are each hydrogen.

6. A compound according to claims 1, 2 or 3 wherein $R_4$ is a straight or branched chain alkyl group having 1 to 5 carbon atoms.

7. A compound according to claim 6 wherein $R_1$ and $R_2$ are hydrogen.

8. A compound according to claim 4 which is 4-(4,10-dihydro-4-oxothieno[2,3-c][1]benzoxepin-6-yl)butyl trifluoroacetate.

9. A compound according to claim 4 which is 4-(4,10-dihydro-4-oxothieno[2,3-c][1]benzoxepin-6-yl)butanol.

10. A compound which is 4-(4,10-dihydro-10-oxothieno[3,2-c][1]benzoxepin-8-yl)pentyl trifluoroacetate.

11. A compound which is 4-(4,10-dihydro-10-oxothieno[3,2-c][1]benzoxepin-8-yl)pentanol.

12. A compound of the formula

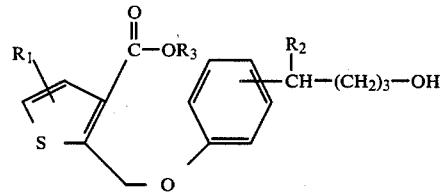

wherein $R_1$ is hydrogen or a straight or branched chain alkyl group having 1 to 5 carbon atoms, $R_2$ is hydrogen or a straight chain alkyl group having 1 to 5 carbon atoms and $R_3$ is hydrogen or straight chain alkyl group having 1 to 5 carbon atoms.

13. A compound according to claim 12 which comprises

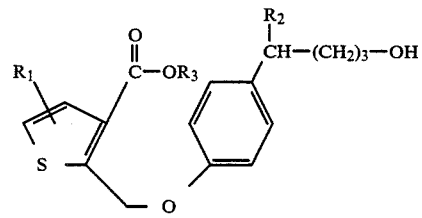

wherein $R_1$, $R_2$ and $R_3$ are as defined.

14. A compound according to claim 12 which comprises

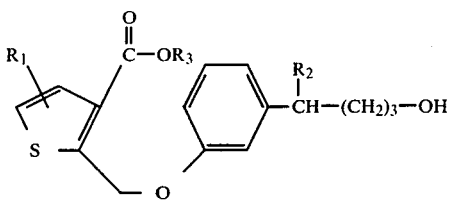

wherein $R_1$, $R_2$ and $R_3$ are as defined.

15. A compound according to claims 12, 13 or 14 wherein $R_1$ and $R_2$ are each hydrogen.

16. The compound according to claim 14 which is 2-[4-(4-hydroxybutyl)phenoxymethyl]-3-thiophenecarboxylic acid methyl ester.

17. The compound according to claim 14 which is 2-[4-(4hydroxybutyl)phenoxymethyl]-3-thiophenecarboxylic acid.

18. A compound of the formula

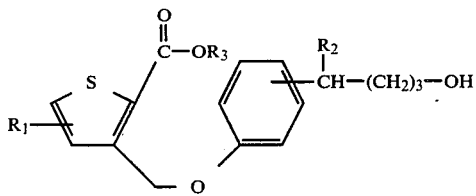

wherein $R_1$ is hydrogen or a straight or branched chain alkyl group having 1 to 5 carbon atoms, $R_2$ is hydrogen or a straight chain alkyl group having 1 to 5 carbon atoms and $R_3$ is hydrogen or a straight chain alkyl group having 1 to 5 carbon atoms.

19. A compound according to claim 18 which comprises

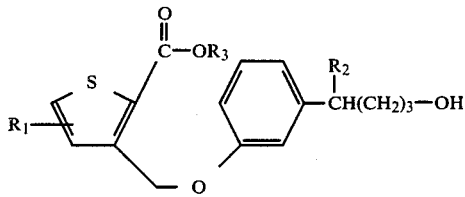

wherein $R_1$, $R_2$ and $R_3$ are as defined.

20. A compound according to claim 18 which comprises

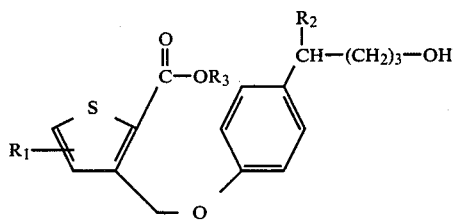

wherein $R_1$, $R_2$ and $R_3$ are as defined.

21. A compound according to claims 18, 19 or 20 wherein $R_1$ and $R_2$ are hydrogen.

22. The compound according to claim 20 which is 4-[4-(2carbomethoxy-3-thienylmethoxy)phenyl]pentanol.

23. The compound according to claim 20 which is 4-[4-(2-carboxy-3-thienylmethoxy)phenyl]pentanol.

24. A method of alleviating pain in a mammal by administering to a mammal a pain-alleviating effective amount of a compound having long duration of action and low ulcerogenicity, wherein said compound has the formula

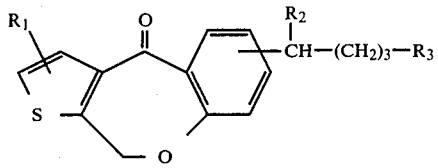

wherein $R_1$ is hydrogen or a straight chain or branched chain alkyl group having 1 to 5 carbon atoms, $R_2$ is hydrogen or a straight chain alkyl group having 1 to 5 carbon atoms; and $R_3$ is OH or

wherein $R_4$ is a straight chain or branched chain alkyl group having 1 to 10 carbon atoms, phenyl or trifluoromethyl.

25. A method according to claim 24 wherein $R_3$ is

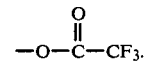

26. A method according to claim 24 wherein $R_1$ and $R_2$ are each hydrogen.

27. A method according to claim 24 wherein $R_3$ is OH.

28. A method according to claim 27 wherein $R_1$ and $R_2$ are each hydrogen.

29. A method of alleviating inflammation in a mammal by administering to a mammal an inflammation-alleviating effective amount of a compound having long duration of action and low ulcerogenicity, wherein said compound has the formula

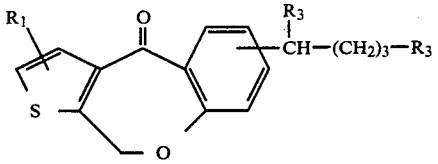

wherein $R_1$ is hydrogen or a straight or branched chain alkyl group having 1 to 5 carbon atoms, and $R_3$ is OH or

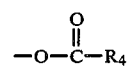

wherein $R_4$ is a straight chain or branched chain alkyl group having 1 to 10 carbon atoms, phenyl or trifluoromethyl.

30. A method according to claim 29 wherein $R_3$ is

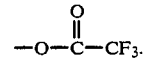

31. A method according to claim 30 wherein $R_1$ and $R_2$ are each hydrogen.

32. A method according to claim 29 wherein $R_3$ is OH.

33. A method according to claim 32 wherein $R_1$ and $R_2$ are each hydrogen.

34. An antiinflammatory composition comprising an inflammatory alleviating effective amount of a compound according to claim 1.

35. An analgesic composition comprising a pain-alleviating effective amount of a compound according to claim 1 and a pharmaceutically acceptable carrier therefor.

36. A process for the preparation of a compound of the formula

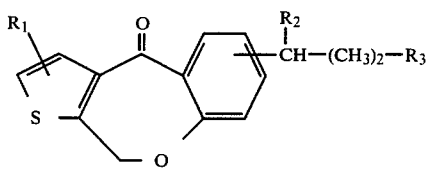

wherein $R_1$ is hydrogen, a straight or branched chain alkyl group of 1 to 5 carbon atoms or halogen; $R_2$ is hydrogen or a straight chain alkyl group of 1 to 5 carbon atoms; and $R_3$ is

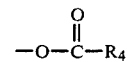

wherein $R_4$ is trifluoromethyl, which comprises contacting a compound of the formula

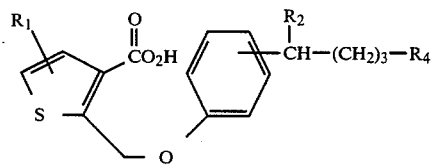

wherein $R_4$ is hydroxyl, with trifluoroacetic anhydride.

37. The process of claim 36 wherein the reaction is conducted in a solvent.

38. The process of claim 37 wherein the solvent is dichloromethane or chloroform.

39. The process of claim 36 wherein the reaction is conducted at temperatures from about ambient to the reflux temperature of the solvent.

40. The process of claim 36 wherein the reaction is conducted at the reflux temperature of trifluoroacetic anhydride.

* * * * *